United States Patent [19]

Jaeggi et al.

[11] Patent Number: 4,939,130
[45] Date of Patent: Jul. 3, 1990

[54] SUBSTITUTED ALKANEDIPHOSPHONIC ACIDS AND PHARMACEUTICAL USE

[75] Inventors: Knut A. Jaeggi, Basel; Leo Widler, Müchenstein, both of Switzerland

[73] Assignee: Ciba-Geigy Corporation, Ardsley, N.Y.

[21] Appl. No.: 315,962

[22] Filed: Feb. 27, 1989

Related U.S. Application Data

[63] Continuation-in-part of Ser. No. 120,284, Nov. 13, 1987, abandoned.

[30] Foreign Application Priority Data

Nov. 21, 1986 [CH] Switzerland .................. 4666/86

[51] Int. Cl.$^5$ .................. A61K 31/675; C07F 9/65
[52] U.S. Cl. .................. 514/94; 514/92; 514/93; 548/112; 548/119
[58] Field of Search .................. 548/119, 112; 514/92, 514/93, 94

[56] References Cited

U.S. PATENT DOCUMENTS

| | | | |
|---|---|---|---|
| 4,503,049 | 3/1985 | Biere et al. | 514/80 |
| 4,687,767 | 8/1987 | Bosies et al. | 514/89 |
| 4,777,163 | 10/1988 | Bosies et al. | 514/80 |

FOREIGN PATENT DOCUMENTS

| | | |
|---|---|---|
| 0084822 | 8/1983 | European Pat. Off. . |
| 186405 | 7/1986 | European Pat. Off. . |
| 0258618 | 3/1988 | European Pat. Off. . |
| 3203307 | 7/1983 | Fed. Rep. of Germany . |
| 3428524 | 2/1986 | Fed. Rep. of Germany . |

OTHER PUBLICATIONS

CA 105:134140r (1986).

*Primary Examiner*—Richard L. Raymond
*Attorney, Agent, or Firm*—JoAnn Villamizar

[57] ABSTRACT

Alkanediphosphonic acids, in particular heteroarylalkanediphosphonic acids of formula

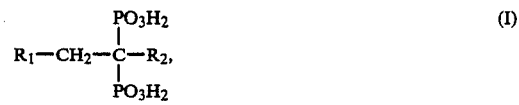

wherein $R_1$ is a 5-membered heteroaryl radical which may be fused with benzene or cyclohexene nuclei and which contains, as hetero atoms, 2 to 4 N-atoms or 1 or 2 N-atoms as well as 1 O- or S-atom, and which is unsubstituted or C-substituted by lower alkyl, phenyl or phenyl which is substituted by lower alkyl, lower alkoxy and/or halogen, or by lower alkoxy, hydroxy, di-lower alkylamino, lower alkylthio and/or halogen, and/or is N-substituted at a N-atom which is capable of substitution by lower alkyl, lower alkoxy and/or halogen, and $R_2$ is hydrogen, hydroxy, amino, lower alkylthio or halogen, and salts thereof, have regulatory action on calcium metabolism and can be used as medicaments for the treatment of diseases associated with impairment of calcium metabolism. The compounds are obtained for example by converting, in a compound of formula

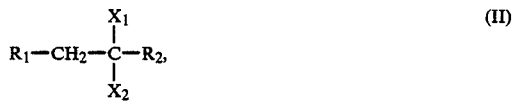

wherein $X_1$ is a functionally modified phosphono group and $X_2$ is a free or functionally modified phosphono group, $X_1$ and, if appropriate $X_2$, into the free phosphono group.

5 Claims, No Drawings

SUBSTITUTED ALKANEDIPHOSPHONIC ACIDS AND PHARMACEUTICAL USE

This is a Continuation-in-Part-Application of our patent application Ser. No. 07/120,284, filed November 13, 1987, now abandoned.

The present invention relates to novel substituted alkanediphosphonic acids, in particular to heteroarylalkanediphosphonic acids of formula

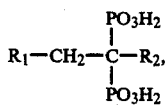

wherein $R_1$ is a 5-membered heteroaryl radical which contains, as hetero atoms, 2 to 4 N-atoms or 1 or 2 N-atoms as well as 1 O- or S-atom, and which is unsubstituted or C-substituted by lower alkyl, phenyl or phenyl which is substituted by lower alkyl, lower alkoxy and/or halogen, or by lower alkoxy, hydroxy, di-lower alkylamino, lower alkylthio and/or halogen, and/or is N-substituted at a N-atom which is capable of substitution by lower alkyl, lower alkoxy and/or halogen, and $R_2$ is hydrogen, hydroxy, amino, lower alkylthio or halogen, and to the salts thereof, to the preparation of said compounds, to pharmaceutical compositions containing them, and to the use thereof as medicaments.

Examples of 5-membered heteroaryl radicals containing 2 to 4 N-atoms or 1 or 2 N-atoms as well as 1 O- or S-atom as hetero atoms are: imidazolyl, e.g. imidazol-1-yl, imidazol-2-yl or imidazol-4-yl, pyrazolyl, e.g. pyrazol-1-yl or pyrazol-3-yl, thiazolyl, e.g. thiazol-2-yl or thiazol-4-yl, or, less preferably, oxazolyl, e.g. oxazol-2-yl or oxazol-4-yl, isoxazolyl, e.g. isooxazol-3-yl or isooxazol-4-yl, triazolyl, e.g. 1H-1,2,4-triazol-1-yl, 4H-1,2,4-triazol-3-yl or 4H-1,2,4-triazol-4-yl or 2H-1,2,3-triazol-4-yl, tetrazolyl, e.g. tetrazol-5-yl, thiadiazolyl, e.g. 1,2,5-thiadiazol-3-yl, and oxdiazolyl, e.g. 1,3,4-oxadiazol-2-yl. These radicals may contain one or more identical or different, preferably one or two identical or different, substituents selected from the group mentioned at the outset. Radicals $R_1$, unsubstituted or substituted as indicated, are e.g. imidazol-2-yl or imidazol-4-yl radicals which are unsubstituted or C-substituted by phenyl or phenyl which is substituted as indicated, or which are C- or N-substituted by $C_1$–$C_4$alkyl, e.g. methyl, and are typically imidazol-2-yl, 1-$C_1$–$C_4$alkylimidazol-2-yl such as 1-methylimidazol-2-yl, or 2- or 5-$C_1$–$C_4$alkylimidazol-4-yl such as 2- or 5-methylimidazol-4-yl, unsubstituted thiazolyl radicals, e.g. thiazol-2-yl, or 1H-1,2,4-triazol radicals, unsubstituted or substituted by $C_1$–$C_4$alkyl such as methyl, e.g. 1-$C_1$–$C_4$alkyl-1H-1,2,4-triazol-5-yl such as 1-methyl-1H-1,2,4-triazol-5-yl, or imidazol-1-yl, pyrazolyl-1-yl, 1H-1,2,4-triazol-1-yl, 4H-1,2,4-triazol-4-yl or tetrazol-1-yl radicals, unsubstituted or C-substituted by phenyl or phenyl which is substituted as indicated or by $C_1$–$C_4$alkyl such as methyl, for example imidazol-1-yl, 2-, 4- or 5-$C_1$–$C_4$alkylimidazol-1-yl such as 2-, 4- or 5-methylimidazol-1-yl, pyrazol-1-yl, 3- or 4-$C_1$–$C_4$alkyl-pyrazol-1-yl such as 3- or 4-methylpyrazol-1-yl, 1H-1,2,4-tetrazol-1-yl, 3-$C_1$–$C_4$alkyl-1H-1,2,4-triazol-1-yl such as 3-methyl-1H-1,2,4-triazol-1-yl, 4H-1,2,4-triazol-1-yl, 3-$C_1$–$C_4$alkyl-4H-1,2,4-triazol-4-yl such as 3-methyl-4H-1,2,4-triazol-4-yl or 1H-1,2,4-tetrazol-1-yl.

Radicals and compounds hereinafter qualified by the term "lower" will be understood as meaning typically those containing up to 7 carbon atoms inclusive, preferably up to 4 carbon atoms inclusive. The general terms have for example the following meanings:

Lower alkyl is for example $C_1$–$C_4$alkyl such as methyl, ethyl, propyl or butyl, and also isobutyl, sec-butyl or tert-butyl, and may further be $C_5$–$C_7$alkyl such as pentyl, hexyl or heptyl.

Phenyl-lower alkyl is for example phenyl-$C_1$–$C_4$alkyl, preferably 1-phenyl-$C_1$–$C_4$alkyl such as benzyl.

Lower alkoxy is for example $C_1$–$C_4$alkoxy such as methoxy, ethoxy, propoxy, isopropoxy, butoxy, isobutoxy, sec-butoxy or tert-butoxy.

Di-lower alkylamino is for example di-$C_1$–$C_4$alkylamino such as dimethylamino, diethylamino, N-ethyl-N-methylamino, dipropylamino, N-methyl-N-propylamino or dibutylamino.

Lower alkylthio is for example $C_1$–$C_4$alkylthio such as methylthio, ethylthio, propylthio or butylthio, and also isobutylthio, sec-butylthio or tert-butylthio.

Halogen is for example halogen having an atomic number of up to 35 inclusive, such as fluorine, chlorine or bromine.

Salts of compounds of formula I are in particular the salts thereof with pharmaceutically acceptable bases, such as non-toxic metal salts derived from metals of groups Ia, Ib, IIa and IIb, e.g. alkali metal salts, preferably sodium or potassium salts, alkaline earth metal salts, preferably calcium or magnesium salts, copper, aluminium or zinc salts, and also ammonium salts with ammonia or organic amines or quaternary ammonium bases such as free or C-hydroxylated aliphatic amines, preferably mono-, di- or tri-lower alkylamines, e.g. methylamine, ethylamine, dimethylamine or diethylamine, mono-, di- or tri(hydroxy-lower alkyl)amines such as ethanolamine, diethanolamine or triethanolamine, tris(-hydroxymethyl)aminomethane or 2-hydroxy-tert-butylamine, or N-(hydroxy-lower alkyl)-N,N-di-lower alkylamines or N-(polyhydroxy-lower alkyl)-N-lower alkylamines such as 2-(dimethylamino)ethanol or D-glucamine, or quaternary aliphatic ammonium hydroxides, e.g. with tetrabutylammonium hydroxide.

In this connection it should also be mentioned that the compounds of formula I may also be obtained in the form of inner salts, provided the group $R_1$ is sufficiently basic. These compounds can therefore also be converted into the corresponding acid addition salts by treatment with a strong protic acid such as a hydrohalic acid, sulfuric acid, sulfonic acid, e.g. methanesulfonic acid or p-toluenesulfonic acid, or sulfamic acid, e.g. N-cyclohexylsulfamic acid.

The compounds of formula I and salts thereof have valuable pharmacological properties. In particular, they have a pronounced regulatory action on the calcium metabolism of warm-blooded animals. Most particularly, they effect a marked inhibition of bone resorption in rats, as can be demonstrated in the experimental procedure described in Acta Endrocinol. 78, 613–24 (1975), by means of the PTH-induced increase in the serum calcium level after subcutaneous administration of doses in the range from about 0.01 to 1.0 mg/kg, as well as in the TPTX (thyroparathyroidectomised) rat model by means of hypercalcaemia induced by vitamin $D_3$ after subcutaneous administration of a dose of about 0.0003 to 1.0 mg. Tumor calcaemia induced by Walker 256 tumors is likewise inhibited after peroral administration of about 1.0 to 100 mg/kg. In addition, when administered subcutaneously in a dosage of about 0.001 to 1.0 mg/kg in the experimental procedure according to Newbould, Brit. J. Pharmacology 21, 127 (1963), and according to Kaibara et al., J. Exp. Med. 159, 1388–96 (1984), the compounds of formula I and salts thereof effect a marked inhibition of the progression of arthritic conditions in rats with adjuvant arthritis. They are therefore eminently suitable for use as medicaments for the treatment of diseases which are associated with impairment of calcium metabolism, for example inflammatory conditions in joints, degenerative processes in articular cartilege, of osteoporosis, periodontitis, hyperparathyroidism, and of calcium deposits in blood vessels or prothetic implants. Favourable results are also achieved in the treatment of diseases in which an abnormal deposit of poorly soluble calcium salts is observed, as in arthritic diseases, e.g. ancylosing spondilitis, neuritis, bursitis, periodontitis and tendinitis, fibrodysplasia, osteoarthrosis or arteriosclerosis, as well as those in which an abnormal decomposition of hard body tissue is the principal symptom, e.g. heriditary hypophosphatasia, degenerative states of articular cartilege, osteoporosis of different provenance, Paget's disease and osteodystrophia fibrosa, and also osteolytic conditions induced by tumors.

The invention relates in particular to compounds of formula I, wherein $R_1$ is an imidazolyl, pyrazolyl, 2H-1,2,3-triazolyl, 1H-1,2,4-triazolyl or 4H-1,2,4-triazolyl, tetrazolyl, oxazolyl, isoxazolyl, oxadiazolyl, thiazolyl or thiadiazolyl radical which is unsubstituted or C-substituted by one or two members selected from lower alkyl, lower alkoxy, phenyl or phenyl which is in turn substituted by one or two members selected from lower alkyl, lower alkoxy and/or halogen, hydroxy, di-lower alkylamino, lower alkylthio and/or halogen, and/or is N-substituted at a N-atom which is capable of substitution by lower alkyl or phenyl-lower alkyl which is unsubstituted or substituted by one or two members selected from lower alkyl, lower alkoxy and/or halogen; and $R_2$ is hydrogen, hydroxy, amino, lower alkylthio or halogen, and salts thereof, especially the inner salts and pharmaceutically acceptable salts thereof with bases.

The invention related more particularly for example to compounds of formula I, wherein $R_1$ is an imidazolyl, pyrazolyl, 2H-1,2,3-triazolyl or 4H-1,2,4-triazolyl, tetrazolyl, oxazolyl, isoxazolyl, oxadiazolyl, thiazolyl or thiadiazolyl radical which is unsubstituted or C-substituted by one or two members selected from lower alkyl, lower alkoxy, phenyl or phenyl which is in turn substituted by one or two members selected from lower alkyl, lower alkoxy and/or halogen, hydroxy, di-lower alkylamino, lower alkylthio and/or halogen, and/or is N-substituted at a N-atom which is capable of substitution by lower alkyl or phenyl-lower alkyl which is unsubstituted or substituted by one or two members selected from lower alkyl, lower alkoxy and/or halogen; and $R_2$ is hydrogen, hydroxy, amino, lower alkylthio or halogen, and salts thereof, especially the inner salts and pharmaceutically acceptable salts thereof with bases.

The invention relates most particularly to compounds of formula I, wherein $R_1$ is an imidazolyl radical, such as imidazol-1-yl, imidazol-2-yl or imidazol-4-yl, a 4H-1,2,4-triazolyl radical such as 4H-1,2,4-triazol-4-yl, or a thiazolyl radical such as thiazol-2-yl, which radical is unsubstituted or C-substituted by one or two members selected from $C_1$–$C_4$alkyl such as methyl, $C_1$–$C_4$alkoxy such as methoxy, phenyl, hydroxy, di-$C_1$–$C_4$alkylamino such as dimethylamino or diethylamino, $C_1$–$C_4$alkylthio such as methylthio, and/or halogen having an atomic number up to 35 inclusive such as chlorine, and/or is N-substituted at a N-atom which is capable of substitution by $C_1$–$C_4$alkyl such as methyl, or phenyl-$C_1$–$C_4$alkyl such as benzyl; and $R_2$ is preferably hydroxy or, less preferably, hydrogen or amino, and salts thereof, especially the inner salts and pharmaceutically acceptable salts thereof with bases.

The invention preferably relates on the one hand to compound of formula I, wherein $R_1$ is an imidazol-2- or -4-yl radical which is unsubstituted or C-substituted by phenyl or C- or N-substituted by $C_1$–$C_4$alkyl such as methyl, e.g. imidazol-2-yl, 1-$C_1$–$C_4$alkylimidazol-2-yl such as 1-methylimidazol-2-yl, or 2- or 5-$C_1$–$C_4$alkylimidazol-4-yl such as 2- or 5-methylimidazol-4-yl, or is an unsubstituted thiazolyl radical, e.g. thiazol-2-yl, or is a 1H-1,2,4-triazolyl radical which is unsubstituted or substituted by $C_1$–$C_4$alkyl such as methyl, e.g. 1$C_1$–$C_4$alkyl-1H-1,2,4-triazol-5-yl such as 1-methyl-1H-1,2,4-triazol-5-yl, and $R_2$ is hydroxy or, less preferably, hydrogen, and salts, especially pharmaceutically acceptable salts, thereof.

The invention preferably relates on the other hand to compounds of formula I, wherein $R_1$ is an imidazol-1-yl, pyrazol-1-yl, 1H-1,2,4-triazol-1-yl, 4H-1,2,4-triazol-4-yl or tetrazol-1-yl radical which is unsubstituted or C-substituted by phenyl or $C_1$–$C_4$alkyl such as methyl, e.g. imidazol-1-yl, 2-, 4- or 5-$C_1$–$C_4$alkylimidazol-1-yl such as 2-, 4- or 5-methylimidazol-1-yl, pyrazol-1-yl, 3- or 4-$C_1$–$C_4$alkylpyrazol-1-yl such as 3- or 4-methylpyrazol-1-yl, 1H-1,2,4-tetrazol-1-yl, 3-$C_1$–$C_4$alkyl-1H-1,2,4-triazol-1-yl such as 3-methyl-1H-1,2,4-triazol-1-yl, 4H-1,2,4-triazol-1-yl, 3-$C_1$–$C_4$alkyl-4H-1,2,4-triazol-4-yl such as 3-methyl-4H-1,2,4-triazol-4-yl or 1H-tetrazol-1-yl, and $R_2$ is hydroxy or, less preferably, hydrogen, and salts, especially pharmaceutically acceptable salts, thereof.

The invention relates first and foremost to compounds of formula I, wherein $R_1$ is an imidazolyl radical which is unsubstituted or substituted by $C_1$–$C_4$alkyl such as methyl, e.g. imidazol-1-yl, imidazol-2-yl, 1-methylimidazol-2-yl, imidazol-4-yl or 2- or 5-methylimidazol-4-yl, and $R_2$ is hydroxy or, less preferably, hydrogen, and salts, especially pharmaceutically acceptable salts, thereof.

The invention relates specifically to the compounds of formula I and the salts thereof, especially the inner salts and pharmaceutically acceptable salts thereof with bases mentioned in the Examples.

The invention further relates to a process based on per se known methods for the preparation of compounds of formula I and salts thereof, which process comprises (a) in a compound of formula

wherein $X_1$ is a functionally modified phosphono group and $X_2$ is a free or functionally modified phosphono group, which compound may be temporarily protected at a N-atom of the radical $R_1$ which is capable of substitution, converting $X_1$ and, if appropriate $X_2$, into the free phosphono group; or (b) reacting a compound of formula $$R_1\text{—}CH_2\text{—}X_3 \quad (III),$$

wherein $X_3$ is a carboxy, carbamyl, imino ether, imino ester or cyano group, which compound may be temporarily protected at a N-atom of the radical $R_1$ which is capable of substitution, with phosphorous acid and phosphorus trichloride, and where a start is made from a compound of formula III, wherein $X_3$ is a carbamyl, imino ether, imino ester or cyano group, the subsequent hydrolysis yields a compound of formula I, wherein $R_2$ is amino, and, if desired, converting a resultant compound into another compound of formula I and/or a resultant free compound into a salt or a resultant salt into the free compound or into another salt.

In process variant (a), functionally modified phosphono groups to be converted into phosphono are for example in ester form, preferably in a diester form of formula $-P(=O)(OR)_2$ (IV), wherein OR is e.g. lower alkoxy or a phenoxy group which is unsubstituted or substituted by lower alkyl, lower alkoxy, halogen, trifluoromethyl and/or hydroxy.

The conversion of a functionally modified phosphono group into the free phosphono group is effected in conventional manner by hydrolysis, for example in the presence of a mineral acid such as hydrobromic acid, hydrochloric acid or sulfuric acid, or by reaction with a tri-lower alkylhalosilane, e.g. with trimethylchlorosilane in the presence of sodium iodide, or preferably with trimethyliodosilane or trimethylbromosilane, preferably with cooling, e.g. in the temperature range from about 0° to 25° C.

The starting materials of formula II, wherein $R_2$ is hydroxy or amino, can be prepared for example by reacting a compound of formula $$R_1\text{—}CH_2\text{—}COOH \quad (IIa)$$

or preferably the nitrile or acid chloride thereof, with a suitable triphosphite of formula $P(OR)_3$ (IIb), wherein R is e.g. lower alkyl, in the presence of a tri-lower alkylamine, e.g. triethylamine, to give an intermediate, presumably a compound of formula

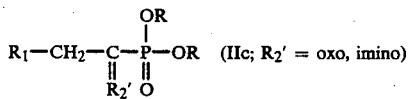
(IIc; $R_2' = $ oxo, imino)

and subsequently reacting said compound with a diphosphite of formula $H\text{—}P(=O)(OR)_2$ (IId) or $P(OH)(OR)_2$ (IIe), wherein R is e.g. lower alkyl, in the presence of a di-lower alkylamine, e.g. diethylamine, or of an alkali metal lower alkanolate, e.g. sodium methanolate, to the corresponding compound of formula

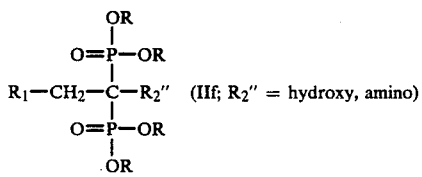
(IIf; $R_2'' = $ hydroxy, amino)

Compounds of formula IIa are obtained for example by converting a suitable compound of formula $$R_1\text{—}CH_3 \quad (IIIa)$$

with a strong base, for example one of the metal bases mentioned in process variant (a), into the carbeniate salt, and reacting said salt with carbon dioxide, or by converting a compound of formula $$R_1\text{—}CH_2\text{—}Y \quad (IIg)$$

wherein Y is reactive esterified hydroxy, preferably halogen such as bromine, with an alkali metal cyanide, e.g. with sodium or potassium cyanide, into the corresponding nitrile (IIg; Y=CN), and hydrolysing the nitrile to the acid, preferably under basic conditions.

Starting materials II, wherein $R_2$ is hydrogen, are obtained for example by reacting a compound of formula $$R_1\text{—}CH_2\text{—}Y \quad (IIg)$$

wherein Y is reactive esterified hydroxy, preferably halogen such as bromine, in the presence of a metal base such as the hydride, an amide or a hydrocarbon compound of an alkali metal, e.g. sodium hydride, sodium amide, ditrimethylsilyl sodium amide or butyl lithium, with a methane diphosphonate, e.g. of formula

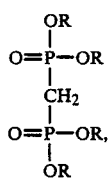
(IIh)

wherein R is for example lower alkyl.

Starting materials of formula II, wherein the radical $R_1$ is bound through a N-atom and $R_2$ is hydrogen or hydroxy, can also be prepared by reacting an appropriate compound of formula $$R_1\text{—}H \quad (IIi).$$

in the presence of a strong metal base such as an alkali metal hydride or an alkaline earth metal hydride, e.g. sodium hydride, with a compound of formula

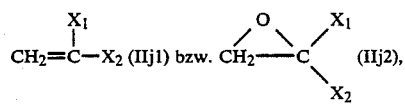
$CH_2=C\text{—}X_2$ (IIj1) bzw. $CH_2\text{—}C$ (IIj2), wherein $X_1$ and $X_2$ are preferably groups of formula IV.

Compounds of formula II, wherein $R_2$ is lower alkylthio or halogen, can be prepared for example starting from the corresponding compounds II, wherein $R_2$ is hydrogen, by converting these with a strong base, e.g. one of those mentioned above, into the carbeniate salt and subsequently reacting said salt with a lower alkylthio donor, for example a di-lower alkyl disulfide or a lower alkanesulfenyl chloride, or with a halogen donor, for example a halogen such as chlorine or bromine, perchloryl fluoride ($FClO_3$) or the like.

In starting materials of formula III for process variant (b), imino ether and imino ester groups are for example those of formula —C(=NH)-X$_3'$ (III'), wherein X$_3'$ is etherified or esterified hydroxy such as lower alkoxy, a phenoxy group, lower alkanoyloxy, a benzoyloxy group or a halogen atom, e.g. a chlorine atom. Compounds of formula III, wherein X$_3$ is a group of formula III', can also be in the form of salts such as mineral acid salts, e.g. hydrohalides.

The reaction of compounds of formula III with phosphorous acid and phosphorus trichloride is carried out in conventional manner, such that the phosphorous acid component is preferably formed in situ by reacting excess phosphorus trichloride with aqueous phosphoric acid, e.g. with commercial phosphoric acid having a strength of about 75 to 95%, preferably of about 85%. The reaction is conveniently carried out with heating, e.g. in the temperature range from about 70° to 120° C., in a suitable solvent such as tetrachloroethane, trichloroethane, chlorobenzene, chlorotoluene or paraffin oil, and with working up by hydrolysis.

The starting materials of formula III, if not known, can be prepared for example by converting an appropriate compound of formula

    

$$R_1—CH_3 \qquad (IIIa)$$

with a strong base, for example with one of the metal bases mentioned in process variant (a), into the carbeniate salt and reacting said salt with carbon dioxide or with a compound of formula Y-X$_3$ (IIIb), wherein Y is halogen such as chlorine or bromine, e.g. with a carbamyl halide, imino ether halide or, preferably, with a cyanogen halide such as cyanogen chloride.

For the temporary protection of a N-atom of the radical R$_1$ which is capable of substitution there may be suitably employed the customary N-protective groups and methods of introducing and removing same, for example di-lower alkoxymethyl groups such as dimethoxymethyl, which can be removed by treatment with an acid, and 2,2,2-trihaloethoxycarbonyl radicals such as 2,2,2-triiodo-, 2,2,2-tribromo- or 2,2,2-trichloroethoxycarbonyl radicals, which may be removed for example by treatment with zinc in acetic acid, α-phenyl-lower alkoxycarbonyl radicals such as carbobenzoxy or trityl, which can be removed for example by catalytic hydrogenation, as well as lower alkanesulfonyl groups such as methanesulfonyl, which can be removed for example by treatment with bis(2-methoxyethoxy) sodium aluminium hydride; and also α-phenylalkyl or alkyl groups, the removal of which will be discussed below.

Compounds of formula I obtained by the process of this invention or by other per se known processes can be converted into other compounds of formula I in a manner known per se.

Thus, for example, compounds of formula I, wherein R$_2$ is amino, can be converted by treatment with nitrous acid into the corresponding compounds of formula I', wherein R$_2$ is hydroxy. The treatment with nitrous acid is effected in conventional manner with formation of same in aqueous solution from a salt thereof, e.g. from sodium nitrite, by treatment with an acid, e.g. hydrochloric acid, to form a corresponding unstable diazonium salt as intermediate, e.g. diazonium chloride, which splits off nitrogen upon introduction of the α-hydroxy group.

In compounds of formula I, wherein the radical R$_1$ is N-substituted by lower alkyl or by phenyl-lower alkyl which is unsubstituted or substituted by lower alkyl, lower alkoxy and/or halogen, it is also possible to remove the N-sustituent: lower alkyl for example by treatment with a haloformate such as a lower alkyl bromoformate or lower alkylchloroformate, and subsequent hydrolysis of the resultant carbamate, and α-phenyl-lower alkyl radicals by hydrogenolysis, e.g. treatment with hydrogen in the presence of a hydrogenation catalyst, e.g. palladium on carbon and/or platinum oxide, or by reduction with a metal, e.g. treatment with an alkali metal in ammonia.

Free compounds of formula I, including the inner salts thereof of formula I, can be converted into basic salts by partial or complete neutralisation with one of the bases mentioned at the outset. In similar manner, it is also possible to convert acid addition salts into the corresponding free compounds or their inner salts.

Conversely, free compounds of formula I can be converted into acid addition salts of formula I'' by treatment with one of the protic acids mentioned at the outset.

Salts can be converted in a manner known per se into the free compounds, for example by treatment with an acid reagent such as a mineral acid, or a base, e.g. an alkali metal hydroxide solution.

The compounds, including their salts, can also be obtained in the form of hydrates or may contain the solvent used for crystallisation in their crystal structure.

Because of the close relationship between the novel compounds in the free form and in the form of their salts, the references made throughout this specification to the free compounds and their salts also apply by analogy to the corresponding salts and free compounds.

The invention also relates to those embodiments of the process in which a compound obtainable as intermediate at any stage of the process is used as starting material and the remaining steps are carried out, or a starting material is used in the form of a salt or, preferably, is formed under the reaction conditions.

In the process of this invention it is preferred to use those starting materials that result in the compounds described at the outset as being especially preferred. Novel starting materials and processes for the preparation thereof likewise constitute further objects of the invention.

The pharmaceutical compositions which contain the compounds of formula I, or pharmaceutically acceptable non-toxic salts thereof, are those for enteral such as oral, or rectal and parenteral, administration to warm-blooded animals, the pharmacological active ingredient being present alone or together with a pharmaceutically suitable carrier.

The novel pharmaceutical compositions contain e.g. from about 10 to 80%, preferably from about 20 to 60%, of the active ingredient. Pharmaceutical compositions for enteral or parenteral administration are e.g. those in dosage unit forms such as dragées, tablets, capsules or suppositories, as well as ampoules. These pharmaceutical compositions are prepared in a manner known per se, for example by conventional mixing, granulating, confectioning, dissolving or lyophilising methods. For example, pharmaceutical compositions for oral administration can be obtained by combining the active ingredient with solid carriers, optionally granulating a resulting mixture and processing the mixture or granulate, if desired or necessary after the addition of suitable excipients, to tablets or dragée cores.

Suitable carriers are in particular fillers such as sugar, for example lactose, saccharose, mannitol or sorbitol, cellulose preparations and/or calcium phosphates, e.g.

tricalcium phosphate or calcium biphosphate, and also binders such as starch pastes, e.g. maize, corn, rice or potato starch, gelatin, tragacanth, methyl cellulose and/or polyvinylpyrrolidone, and/or, if desired, disintegrators, such as the abovementioned starches, also carboxymethyl starch, crosslinked polyvinylpyrrolidone, agar, alginic acid or a salt thereof such as sodium alginate. Excipients are in particular glidants and lubricants, for example silica, talcum, stearic acid or salts thereof such as magnesium stearate or calcium stearate, and/or polyethylene glycol. Dragée cores are provided with suitable coatings which can be resistant to gastric juices, using inter alia concentrated sugar solutions which may contain gum arabic, talcum, polyvinylpyrrolidone, polyethylene glycol and/or titanium dioxide, shellac solutions in suitable organic solvents or mixtures of solvents or, for the preparation of coatings which are resistant to gastric juices, solutions of suitable cellulose preparations such as acetyl cellulose phthalate or hydroxypropyl methyl cellulose phthalate. Dyes or pigments can be added to the tablets or dragée coatings, for example to identify or indicate different doses of active ingredient.

Further pharmaceutical compositions for oral administration are dry-filled capsules made of gelatin and also soft sealed capsules consisting of gelatin and a plasticiser such as glycerol or sorbitol. The dry-filled capsules can contain the active ingredient in the form of granules, for example in admixture with fillers such as lactose, binders such as starches, and/or glidants such as talcum or magnesium stearate, and optionally stabilisers. In soft capsules, the active ingredient is preferably dissolved or suspended in a suitable liquid, such as a fatty oil, paraffin oil or a liquid polyethylene glycol, to which a stabiliser can also be added.

Suitable pharmaceutical compositions for rectal administration are e.g. suppositories, which consist of a combination of the active ingredient with a suppository base. Examples of suitable suppository bases are natural or synthetic triglycerides, paraffin hydrocarbons, polyethylene glycols and higher alkanols. It is also possible to use gelatin rectal capsules which contain a combination of the active ingredient with a base material. Suitable base materials are e.g. liquid triglycerides, polyethylene glycols and paraffin hydrocarbons.

Particularly suitable dosage forms for parenteral administration are aqueous solutions of an active ingredient in water-soluble form, for example a water-soluble salt, and also suspensions of the active ingredient, such as corresponding oily injection suspensions, for which there are used suitable lipophilic solvents or vehicles such as fatty oils, for example sesame oil, or synthetic fatty acid esters, for example ethyl oleate or triglycerides, or aqueous injection suspensions which contain substances which increase the viscosity, for example sodium carboxymethyl cellulose, sorbitol and/or dextran, and optionally also stabilisers.

The present invention also relates to the use of the compounds of formula I and salts thereof preferably for the treatment of inflammatory conditions, primarily to diseases associated with impairment of calcium metabolism, e.g. rheumatic diseases and, in particular, osteoporoses.

Doses below 0.001 mg/kg of body weight affect pathological sclerosis and the decomposition of hard tissue only insignificantly. Long-term toxic side-effects may occur at doses of over 100 mg/kg of body weight. The compounds of formula I and salts thereof can be administered orally, as well as subcutaneously, intramuscularly or intravenously in hypertonic solution. Preferred daily doses are, for oral administration, in the range from about 0.1 to 5 mg/kg, for subcutaneous and intramuscular administration in the range from about 0.1 to 1 mg/kg and, for intravenous administration, in the range from about 0.01. to 2 mg/kg.

The dosage of the compounds of formula I and salts thereof is, however, variable and depends on the respective conditions such as the nature and severity of the illness, the duration of treatment and on the respective compound. Single doses contain for example from 0.01 to 10 mg; dosage unit form for parenteral, e.g. intravenous, administration contain e.g. from 0.01 to 0.1 mg, preferably from 0.02 to 0.08 mg; and oral dosage unit forms contain e.g. from 0.2 to 2.5 mg, preferably from 0.3 to 1.5 mg per kg of body weight. The preferred single dose for oral administration is from 10 to 100 mg and, for intravenous administration, from 0.5 to 5 mg. It is, however, possible to administer up to four single doses daily. The higher doses for oral administration are necessary on account of the limited absorption. In prolonged treatment, the dosage can normally be reduced to a lower level after an initially higher dosage in order to maintain the desired effect.

The following Examples illustrate the invention without in any way limiting the scope thereof.

EXAMPLE 1

With stirring and under reflux, 8.6 g (0.053 mole) of imidazol-4-ylacetic acid hydrochloride, 7.1 ml of 85% phosphoric acid and 25 ml of chlorobenzene are heated to 100° C. Then 13.9 ml of phosphorus trichloride are added dropwise at 100° C., whereupon evolution of gas occurs. Over the course of 30 minutes a dense mass precipitates from the reaction mixture. The batch is heated for 3 hours to 100° C. and the supernatant chlorobenzene is removed by decantation. With stirring and under reflux, the residual viscous mass is heated to the boil for 3 hours with 40 ml of 9N hydrochloric acid. The batch is filtered hot with the addition of carbon and the filtrate is diluted with acetone, whereupon the crude 2-(imidazol-4-yl)-1-hydroxy-ethane-1,1-diphosphonic acid precipitates. This product is recrystallised from water. Melting point: 238°–240° C. (dec.).

EXAMPLE 2

Reaction of 1-methylimidazol-2-ylmethyl bromide, benzylimidazol-2-ylmethyl chloride, (imidazol-1-methyl)toluenesulfonate, imidazol-4-ylmethyl chloride and thiazolyl-2-ylmethyl bromide with tetraethyl methanediphosphonate and hydrolysis of the resultant primary ethanediphosphonates in accordance with Example 9 or 12 also gives 2-(1-methylimidazol-2-yl)ethane-1,1-diphosphonic acid, m.p. 295° C. (dec.); 2-(1-benzylimidazol-2-yl)ethane-1,1-diphosphonic acid monohydrate, m.p. 181°–183° C.; 2-(imidazol-1-yl)ethane-1,1-diphosphonic acid, m.p. 255° C. (dec.); 2-(imidazol-4-yl)ethane-1,1-diphosphonic acid, and 2-(thiazol-2-yl)ethane-1,1-diphosphonic acid, m.p. 259° C. (dec.), and salts thereof, e.g. disodium salts.

EXAMPLE 3

The procedure of Example 1 is repeated, starting from 1-methylimidazol-2-acetic acid hydrochloride, to give 2-(1-methylimidazol-2-yl)-1-hydroxyethane-1,1-diphosphonic acid monohydrate, m.p. 261° C. (dec.).

The starting material can be prepared as follows: 0.5 g (0.032 mole) of 1-methyl-2-cyanomethylimidazole hydrochloride, 15 ml of glacial acetic and 15 ml of 36% hydrochlorid acid are heated for 24 hours to the boil under reflux. The reaction mixture is then evaporated to dryness under reduced pressure and the residue is taken up in 30 ml of hot glacial acetic acid and undissolved ammonium chloride is removed by filtration. The filtrate is concentrated by evaporation and the residue is taken up in acetone, affording 1-methyl-2-carboxymethylimidazole hydrochloride, m.p. 163°–164° C.

EXAMPLE 4

The procedure of Example 1 is repeated, starting from 4(5)-methylimidazol-5(4)-acetic acid hydrochloride, to give 2-[4(5)-methylimidazol-5(4)-yl]-1-hydroxyethane-1,1-diphosphonic acid, m.p. 217°–218° C. (dec.). The starting 4(5)-methylimidazol-5(4)-acetic acid hydrochlroide can be obtained in a manner similar to that described in Example 3.

EXAMPLE 5

The procedure of Example 1 is repeated, starting from 1-benzylimidazol-2-acetic acid hydrochloride and 1-methylimidazol-2-acetic acid hydrochloride, to give respectively 2-(1-benzylimidazol-2-yl)-1-hydroxyethane-1,1-diphosphonic acid of m.p. 171° C. (dec.), and 2-(1-methylimidazol-2-yl)-1-hydroxyethane-1,1-diphosphonic acid monohydrate of m.p. 261° C. (dec.), and salts thereof, e.g. sodium salts. The starting 1-benzylimidazol-2-acetic acid hydrochloric acid, m.p. 124°–125° C., can be obtained in a manner similar to that described in Example 2.

EXAMPLE 6

14.8 g (0.051 mole) of tetraethyl methanediphosphonate are added dropwise to a suspension of 2.4 g of sodium hydride in 35 ml of absolute tetrahydrofuran, and the reaction mixture is stirred at room temperature until the evolution of gas has ceased. Then 11.3 g (0.0465 mole) of 1-benzyl-2-chloromethylimidazole hydrochloride are added in portions. With stirring, the reaction mixture is heated under reflux for 20 hours to the boil. Precipitated sodium chloride is then removed by filtration and the filtrate is concentrated by evaporation under reduced pressure to give crude tetraethyl (1-benzylimidazol-2-ylmethyl)-methanediphosphonate. 3.0 g (0.065 mole) of tetraethyl (1-benzylimidazol-2-ylmethyl)-methanediphosphonate and 12 ml of 36% hydrochloric acid are heated under reflux for 20 hours to the boil. The reaction mixture is then concentrated by evaporation and the residue is crystallised from aqueous methanol, to give 2-(1-benzylimidazol-2-yl)ethane-1,1-diphosphonic acid monohydrate of m.p. 181°–183° C. Yield: 80% of theory.

EXAMPLE 7

Following the procedure of Example 6, reaction of 1-methyl-2-chloromethylimidazole hydrochloride, 1-methyl-5-chloromethyl-1H-1,2,4-triazole hydrochloride, and 2-chloromethylthiazole hydrochloride to the corresponding tetraethyl ethanediphosphonates and subsequent ester cleavage with trimethylbromosilane in the described manner affords: 2-(1-methylimidazol-2-yl)ethane-1,1-diphosphonic acid, m.p. 295° C. (dec.), 2-(1-methyl-1H-1,2,4-triazol-5-yl)ethane-1,1-diphosphonic acid, m.p. 274°–275° C., 2-thiazol-2-yl)ethane-1,1-diphosphonic acid, m.p. 259° C. (dec.), and salts thereof, e.g. disodium salts, and hydrates.

The starting 1-methyl-5-chloromethyl-1H-1,2,4-triazole hydrochloride can be prepared as follows: 11.1 g (0.10 mole) of 5-hydroxymethyl-1-methyl-1H-1,2,4-triazole are dissolved in 25 ml of dichloromethane. While cooling with ice and with stirring, 29.7 g of thionyl chloride are added dropwise. The reaction mixture is then stirred for 1 hour at room temperature and thereafter for 20 minutes at boiling temperature under reflux. The precipitate is filtered with suction, washed with diethyl ether and vacuum dried. Melting point: 136°–137° C.

EXAMPLE 8

The procedure of Example 1 is repeated, starting from 1-imidazoleacetic acid hydrochloride, 1-(1H-1,2,4-triazole)acetic acid hydrochloride and 1-pyrazoleacetic acid hydrochloride, to give the following compounds: 2-(imidazol-1-yl)-1-hydroxyethane-1,1-diphosphonic acid, m.p. 239° C. (dec.), 2-(1H-1,2,4-triazol-1-yl)-1-hydroxyethane-1,1-diphosphonic acid, m.p. 255° C. (dec.) and 2-(pyrazol-1-yl)-1-hydroxyethane-1,1-diphosphonic acid, m.p. 234° C. (dec.).

EXAMPLE 9

3.3 g (0.0072 mole) of tetraethyl 2-(benzylimidazol-2-yl)ethane-1,1-diphosphonate are dissolved in 50 ml of liquid ammonia and, with stirring, 1.0 g of sodium is added gradually in small portions until the blue colour of the solution is maintained for some time. Then 2.35 g of ammonium chloride are added in portions. The ammonia is then removed by evaporation, the residue is taken up in diethyl ether, the solution is filtered and the filtrate is concentrated by evaporation, affording tetraethyl 2-(imidazol-2-yl)ethane-1,1-diphosphonate as a colourless oil.

2.3 g (0.0062 mole) of tetraethyl 2-(imidzol-2-yl)ethane-1,1-diphosphonate are dissolved in 20 ml of methylene chloride. To the solution are added 4.8 ml of trimethylbromosilane and the reaction mixture is allowed to stand for 24 hours at room temperature and then concentrated by evaporation under reduced pressure. The residue is crystallised from 10 ml of methanol and 1 ml of water, to give 2-(imidazol-2-yl)ethane-1,1-diphosphonic acid of m.p. 279°–282° C. (dec.).

EXAMPLE 10

With stirring and under reflux, 8.6 g (0.053 mole) of imidazol-1-ylacetic acid hydrochloride, 7.1 ml of 85% phosphoric acid and 25 ml of chlorobenzene are heated to 100° C. Then 13.9 ml of phosphorus trichloride are added dropwise at 100° C., whereupon evolution of gas occurs. Over the course of 30 minutes a dense mass precipitates from the reaction mixture. The batch is heated for 3 hours to 100° C. and the supernatant chlorobenzene is removed by decantation. The residual viscous mass is heated for 3 hours to the boil, with stirring and under reflux, with 40 ml of 9N hydrochloric acid. The batch is then filtered hot with the addition of carbon and the filtrate is diluted with acetone, whereupon the crude 2-(imidazol-1-yl)-1-hydroxyethane-1,1-diphosphonic acid precipitates. This product is recrystallised from water. Melting point: 239° C. (dec.). Yield: 41% of theory.

EXAMPLE 11

The procedure of Example 9 is repeated, starting from tetraethyl 2-(pyrazol-1-yl)ethane-1,1-diphosphonate and tetraethyl 2-(imidazol-1-yl)ethane-1,1-diphosphonate. Treatment with trimethylbromosilane and working up with aqueous methanol gives 2-(pyrazol-1-yl)ethane-1,1-diphosphonic acid, m.p. 227° C. (dec.), and 2-(imidazol-1-yl)ethane-1,1-diphosphonic acid, m.p. 255° C. (dec.).

The starting esters can be prepared e.g. as follows: 0.10 g of sodium hydride is suspended in 4.0 ml of absolute tetrahydrofuran. A solution of 0.27 g (0.04 mole) of pyrazole in 2.0 ml of tetrahydrofuran is slowly added dropwise to the clear reaction solution are added 1.2 g of tetraethyl vinylidenediphosphonate and the reaction mixture is kept for 24 hours at room temperature. Then 2 ml of 2N ethanolic hydrochloric acid are added. Precipitated sodium chloride is removed by filtration and the filtrate is concentrated by evaporation.

EXAMPLE 12

The procedure of Example 10 is repeated, starting from 0.05 mole of 4H-1,2,4-triazol-2-ylacetic acid, to give 2-(4H-1,2,4-triazol-4-yl)-1-hydroxyethane-1,1-diphosphonic acid of m.p. 255° C. (dec.) and salts thereof, e.g. disodium salts.

EXAMPLE 13

Reaction of (imidazol-1-ylmethyl) p-toluenesulfonate with tetraethyl methanediphosphonate and hydrolysis of the primary ethanediphosphonate in accordance with Example 2 gives 2-(imidazol-1-yl)ethane-1,1-diphosphonic acid of m.p. 255° C. (dec.) and salts thereof, e.g. the disodium salt.

EXAMPLE 14

Following the procedure of Example 3, 1-benzyl-2-carboxymethylimidazole hydrochloride of m.p. 124°–125° C. is obtained from 1-benzyl-2-cyanomethylimidazole.

Following the procedure of Example 10, 2-(1-benzylimidazol-2-yl)-1-hydroxyethane-1,1-diphosphonic acid of m.p. 171° C. (dec.) is obtained from 1-benzyl-2-carboxymethylimidazole hydrochloride.

EXAMPLE 15

3.4 g (0.0094 mole) of 2-(1-benzylimidazol-2-yl)-1-hydroxyethanediphosphonic acid are dissolved in 40 ml of liquid ammonia and then 1 g of sodium is added gradually, with stirring, in small portions until the blue colour of the solution is maintained for some considerable time. Then 2.35 g of ammonium chloride are added in portions. The ammonia is then removed by evaporation, the residue is taken up in 20 ml of hot water, the solution is filtered and then 10 ml of concentrated hydrochloric acid are added to the filtrate. The precipitated crystals are isolated by filtration and recrystallised from aqueous methanol, to give 2-(imidazol-2-yl)-1-hydroxyethanediphosphonic acid of m.p. 235° C. (dec.).

EXAMPLE 16

3.59 g (0.01 mole) of 1-amino-2-(1-benzylimidazol-2-yl)ethane-1,1-diphosphonic acid are dissolved in 20 ml of 1N sodium hydroxide solution, 0.82 g of sodium nitrite is added, and the solution is cooled to 0° C. With stirring, 18 ml of 2N hydrochloric acid are slowly added dropwise. Stirring is continued for 1 hour at 0°–10° C. and the precipitated product is isolated by filtration. Recrystallisation from water gives 2-(1-benzylimidazol-2)-1-hydroxyethane-1,1-disphosphonic acid of m.p. 171° C. (dec.).

EXAMPLE 17

In accordance with the procedures described in Examples 1 to 16 it is also possible to prepare 2-[2-methylimidazol-4(5)-yl]-1-hydroxy-ethane-1,1-diphosphonic acid, m.p. 261°–262° C. (dec.); 2-[2-phenylimidazol-4(5)-yl]-1-hydroxy-ethane-1,1-diphosphonic acid, m.p. 223°–224° C.; 2-(4,5-dimethylimidazol-1-yl)-1-hydroxyethane-1,1-diphosphonic acid, m.p. 251°–252° C., and 2-(2-methylimidazol-1-yl)-1-hydroxyethane-1,1-diphosphonic acid, m.p. 245°–246° C. (dec.), and salts thereof, e.g. disodium salts.

EXAMPLE 18

With stirring and under reflux, 11.95 g of 2-phenylimidazol-4-ylacetic acid hydrochloride, 7.1 ml of 85% phosphoric acid and 25 ml of chlorobenzene are heated to 100° C. Then 13.9 ml of phosphorus trichloride are added dropwise at 100° C., whereupon evolution of gas occurs. Over the course of 30 minutes a dense mass precipitates from the reaction mixture. The batch is heated for 3 hours to 100° C. and the supernatant chlorobenzene is removed by decantation. With stirring and under reflux, the residual viscous mass is heated to the boil for 3 hours with 40 ml of 9N hydrochloric acid. The batch is filtered hot with the addition of carbon and the filtrate is diluted with acetone, whereupon the crude 2-(2-phenylimidazol-4-yl)-1-hydroxyethane-1,1-diphosphonic acid precipitates. This product is recrystallised from water, yielding the sesguihydrate of m.p. 223°–224° C.

EXAMPLE 19

10 ml of 2N aqueous sodium hydroxide solution are added, with stirring, to a suspension of 3,36 g of 2-(2-phenylimidazol-4-yl)-1-hydroxy-ethane-1,1-diphosphonic acid in 10 ml of water. The resulting solution is evaporated to dryness. The residue is triturated with 40 ml of methanol. The crystalline precipitate formed is filtered off and dried yielding disodium 2-(2-phenylimidazol-4-yl)-1-hydroxyethane-1,1-diphosphonate-dihydrate m.p. 281°–283° C. (dec.).

EXAMPLE 20

In an analogous manner as described in Example 19, the following disodium salts can be prepared: disodium 2-(2-methylimidazol-4-yl)-1-hydroxy-ethane-1,1-diphosphonate-monohydrate, m.p. 292°–295° C. (dec.); disodium 2-(2-methylimidazol-1-yl)-1-hydroxy-ethane-1,1-diphosphonate-dihydrate, m.p. 295°–297° C. (dec.); disodium 2-(4,5-dimethylimidazol-1-yl)-1-hydroxyethane-1,1-diphosphonate-dihydrate, m.p. 286°–290° C. (dec.); disodium 2-(imidazol-1-yl)-1-hydroxy-ethane-1,1-diphosphonate-dihydrate, m.p. 291°–293° C. (dec.) and disodium 2-(pyrazol-1-yl)-1-hydroxy-ethane-1,1-diphosphonate-monohydrate, m.p. >300° C. (dec.).

EXAMPLE 21

A solution of 0.121 g of tris(hydroxymethyl)methylamine in 2 ml of water is added to a solution of 0.141 g of 2-(imidazol-1-yl)-1-hydroxy-ethane-1,1-diphosphonic acid in 1 ml of water. The resulting solution is concentrated by evaporation in vacuo and triturated with 6 ml of warm methanol. After cooling, a cristalline precipitate is formed which is filtered off and dried for 1 hour in vacuo at 80° yielding pure mono-tris(hydroxymethyl)methylammonium 2-(imidazol-1-yl)-1-hydroxyethane-1,1-diphosphonate of m.p. 170°–175°.

EXAMPLE 22

In an analogous manner as described in Example 21 the following tris(hydroxymethyl)methylammonium salts can be prepared: di-tris(hydroxymethyl)methylammonium 2-(imidazol-4-yl)-1-hydroxy-ethane-1,1-diphosphonate, m.p. 116°–117° C. (dec.); di-tris(hydroxymethyl)methylammonium 2-(4,5-dimethylimidazol-1-yl)-1-hydroxy-ethane-1,1-diphosphonate-monohydrate m.p. 110°–113° C. (dec.); di-tris(hydroxymethyl)methylammonium 2-(5-methylimidazol-4-yl)-1-hydroxy-ethane-1,1-diphosphonate, m.p. 122°–126° C. (dec.) and di-tris(hydroxymethyl)methylammonium 2-(1-benzylimidazol-1-yl)-1-hydroxy-ethane-1,1-diphosphonate-monohydrate, m.p. >300° C. (dec.).

EXAMPLE 23

Tablets containing 100 mg of active ingredient, e.g. 2-(imidazol-4-yl)-1-hydroxyethane-1,1-diphosphonic acid or a salt thereof, e.g. the disodium salt, can be prepared as follows:

| Composition (for 100 tablets) | |
|---|---|
| active ingredient | 100.0 g |
| lactose | 100.0 g |
| corn starch | 47.0 g |
| magnesium stearate | 3.0 g |

Procedure

All the solid constituents are sieved through a sieve having a mesh size of 0.6 mm. The active ingredient is then mixed with lactose, talcum, magnesium stearate and half of the starch in a suitable mixer. The other half of the starch is suspended in 40 ml of water and the suspension is added to a boiling solution of polyethene glycol in 100 ml of water. The resultant mixture is granulated, if necessary with the further addition of water. The granulate is dried overnight at 35° C., sieved through a sieve having a mesh size of 1.2 mm, and compressed to tablets of 6 mm diameter which are concave on both sides.

In like manner, tablets each containing 100 mg of another compound of formula I obtained in Examples 1–22 can also be prepared which compounds may also be in the form of salts with bases, e.g. as sodium salt.

EXAMPLE 24

Lozenges containing 75 mg of active ingredient, e.g. 2-(imidazol-4-yl)-1-hydroxyethane-1,1-diphosphonic acid or a salt thereof, e.g. the disodium salt, can be prepared as follows:

| Composition (for 100 tablets) | |
|---|---|
| active ingredient | 75.0 g |
| mannitol | 230.0 g |
| lactose | 100.0 g |
| talcum | 21.0 g |
| glycine | 12.5 g |
| stearic acid | 10.0 g |
| saccharine | 1.5 g |
| 5% gelatin solution | q.s. |

Procedure

All solid ingredients are first sieved through a sieve having a mesh size of 0.25 mm. The mannitol and lactose are mixed, the mixture is granulated while adding gelatin solution, sieved through a sieve having a mesh size of 2 mm, dried at 50° C. and once more sieved through a sieve having a mesh size of 1.7 mm. The active ingredient, glycine and saccharine are carefully mixed, then the mannitol, lactose granulate, stearic acid and the talcum are added. All the ingredients are thoroughly mixed and compressed to lozenges having a diameter of about 10 mm which are concave on both sides and provided with a breaking notch on the topside.

In like manner, lozenges containing 75 mg of another compound of formula I obtained in Examples 1–22 can also be prepared, which compounds can also be in the form of salts with bases, e.g. the sodium salt.

EXAMPLE 25

Tablets containing 10 mg of active ingredient, e.g. 2-(imidazol-4-yl)-hydroxyethane-1,1-diphosphonic acid or a salt thereof, e.g. the disodium salt, can be prepared as follows:

| Composition (for 1000 tablets) | |
|---|---|
| active ingredient | 10.0 g |
| lactose | 115.7 g |
| corn starch | 17.5 g |
| polyethylene glycol 6000 | 5.0 g |
| talcum | 5.0 g |
| magnesium stearate | 4.0 g |
| demineralised water | q.s. |

Procedure

The solid constituents are sieved through a sieve having a mesh size of 0.6 mm. The active ingredient is then mixed with lactose, talcum, magnesium stearate and half of the starch in a suitable mixer. The other half of the starch is suspended in 65 ml of water and the suspension is added to a boiling solution of polyethene glycol in 260 ml of water. The resultant paste is added to the powders and granulated, optionally with the further addition of water. The granulate is dried overnight at 35° C., sieved through a sieve having a mesh size of 1.2 mm, and compressed to tablets of 10 mm diameter with a breaking notch on the topside and which are concave on both sides.

In like manner, tablets containing 10 mg of another compound of formula I obtained in examples 1–22 can also be prepared, which compounds can also be in the form of salts with bases, e.g. the sodium salt.

EXAMPLE 26

Hard gelatin capsules containing 100 mg of active ingredient, e.g. 2-(imidazol-4-yl)-1-hydroxyethane-1,1-diphosphonic acid or a salt thereof, e.g. the disodium salt, can be prepared as follows:

| Composition (for 1000 capsules) | |
|---|---|
| active ingredient | 350.0 g |
| microcrystalline cellulose | 30.0 g |
| sodium lauryl sulfate | 2.0 g |
| magnesium stearate | 8.0 g |

The sodium lauryl sulfate is sieved through a sieve having a mesh size of 0.2 mm and added to the active ingredient (lyophilised) and both components are intimately mixed for 10 minutes. Then the microcrystalline cellulose is sieved through a sieve having a mesh size of 0.9 mm, added to the above mixture, and the ingredients are intimately mixed for 10 minutes. Finally, the magnesium is sieved through a sieve having a mesh size of 0.8 mm, added to the mixture, and all the ingredients are mixed for 3 minutes. Size 0 hard gelatin capsules (elongated) are filled with 390 mg of this mixture.

In like manner, capsules containing 100 mg of another compound of formula I obtained in Examples 1-22 can also be prepared, which compounds can also be in the form of salts with bases, e.g. the disodium salt.

EXAMPLE 27

A 0.2% injection or infusion solution can be prepared e.g. as follows:

| | |
|---|---|
| active ingredient, e.g. 2-(imidazol-4-yl)-1-hydroxyethane-1,1-di-phosphonic acid or a salt thereof | 5.0 g |
| sodium chloride | 22.5 g |
| phosphate buffer (pH = 7.4) | 300.0 g |
| demineralised water to make up | 2500.0 ml |

The active ingredient is dissolved in 1000 ml of water and filtered through a microfilter. The buffer solution is added, followed by the addition of water to make up 2500 ml. To prepare dosage unit forms, 1.0 or 2.5 ml of the solution are filled into glass ampoules (each containing 2.0 or 5.0 mg of active ingredient).

What is claimed is:

1. A heteroarylalkanediphosphonic acid of the formula

wherein $R_1$ denotes an 1-imidazolyl or 2-(1-methyl)imidazolyl radical and $R_2$ represents hydroxy, or a salt thereof.

2. A compound as claimed in claim 1 being 2-(imidazol-1-yl)-1-hydroxy-ethane-1,1-diphosphonic acid or a salt thereof.

3. A compound as claimed in claim 1 being 2-(1-methylimidazol-2-yl)-1-hydroxyethane-1,1-diphosphonic acid or a salt thereof.

4. A pharmaceutical composition for the treatment or prophylaxis of diseases associated with impaired calcium metabolism, containing a therapeutically effective amount of a compound claimed in claim 1 in the free form or in a pharmaceutically acceptable salt form, together with conventional pharmaceutical carriers.

5. A method of treating diseases associated with impaired calcium metabolism which comprises administering a therapeutically effective amount of a compound claimed in claim 1 in the free form or in a pharmaceutically acceptable salt form to a warm-blooded animal in need thereof.

* * * * *